US006579513B1

(12) United States Patent
Tashjian et al.

(10) Patent No.: US 6,579,513 B1
(45) Date of Patent: Jun. 17, 2003

(54) HYGIENE MOUTHSPRAY COMPOSITION

(75) Inventors: Anne Tashjian, River Edge, NJ (US); Susan Mills, Ringwood, NJ (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 10/038,544

(22) Filed: Jan. 3, 2002

(51) Int. Cl.$^7$ .............................. A61K 7/16; A61K 7/22
(52) U.S. Cl. ........................................... 424/54; 424/49
(58) Field of Search ...................... 424/49–88

(56) References Cited

U.S. PATENT DOCUMENTS

| | | | |
|---|---|---|---|
| 4,256,730 A | * 3/1981 | Benedict | |
| 4,472,373 A | 9/1984 | Ryan | 424/54 |
| 4,663,154 A | 5/1987 | Ryan | 424/54 |
| 4,774,329 A | 9/1988 | Friedman | 536/103 |
| 4,835,002 A | * 5/1989 | Wolf et al. | 426/590 |
| 4,959,204 A | 9/1990 | Ryan | 424/54 |
| 5,045,337 A | * 9/1991 | El-Nokaly et al. | 426/602 |
| 5,158,763 A | * 10/1992 | Gaffar et al. | |
| 5,236,699 A | 8/1993 | Libin | 424/54 |
| 5,266,306 A | 11/1993 | Ohtsuki et al. | 424/54 |
| 5,286,496 A | 2/1994 | Stapler et al. | 424/490 |
| 5,292,527 A | * 3/1994 | Konopa | 424/54 |
| 5,300,305 A | 4/1994 | Stapler et al. | 42/490 |
| 5,370,864 A | 12/1994 | Peterson et al. | 424/49 |
| 5,382,424 A | 1/1995 | Stapler et al. | 424/54 |
| 5,405,604 A | * 4/1995 | Hall | 424/54 |
| 5,407,664 A | * 4/1995 | Konopa | 424/54 |
| 5,407,665 A | * 4/1995 | McLaughlin et al. | 424/58 |
| 5,451,401 A | * 9/1995 | Zerby et al. | |
| 5,503,822 A | 4/1996 | Schulman | 424/49 |
| 5,560,906 A | 10/1996 | Scodari et al. | 424/54 |
| 5,624,906 A | 4/1997 | Vermeer | 514/23 |
| 5,681,549 A | * 10/1997 | McLaughlin et al. | |
| 5,686,063 A | * 11/1997 | McLaughlin et al. | |
| 6,077,502 A | 6/2000 | Witt et al. | 424/53 |
| 6,077,559 A | * 6/2000 | Logan et al. | 426/650 |
| 6,086,856 A | * 7/2000 | Saferstein et al. | 424/58 |
| 6,117,417 A | 9/2000 | Wicks et al. | 424/54 |
| 6,132,702 A | 10/2000 | Witt et al. | 424/53 |
| 6,159,459 A | 12/2000 | Hunter et al. | 424/78.08 |
| 6,207,192 B1 | * 3/2001 | Lau | 424/486 |
| 6,238,648 B1 | * 5/2001 | Leusch et al. | |
| 6,355,229 B1 | * 3/2002 | Adamy | 424/54 |

FOREIGN PATENT DOCUMENTS

| | | | |
|---|---|---|---|
| EP | 310299 | * | 4/1989 |
| WO | 95 07684 | * | 3/1995 |
| WO | 95 08920 | * | 4/1995 |
| WO | 97 13495 | * | 4/1997 |

* cited by examiner

*Primary Examiner*—Shep K. Rose
(74) *Attorney, Agent, or Firm*—Ohlandt, Greeley, Ruggiero & Perle, LLP

(57) ABSTRACT

The present invention relates to a mouthspray formulation, which reduces oral bacteria and is effective against dental plaque, gingivitis and oral malodor. The preferred formulation has a bactericidal agent with cetyl pyridinium chloride and domiphen bromide, an alcohol, a sweetener component, and a flavor system. The flavor system may also have or more of the following: a flavorant, a humectant, a surfactant, a sweetener, and a colorant agent.

29 Claims, No Drawings

HYGIENE MOUTHSPRAY COMPOSITION

BACKGROUND OF THE INVENTION

1. Field of the Invention

The present invention relates to an oral hygiene composition. In particular, the present invention relates to a mouthspray formulation, which reduces oral bacteria and is effective against plaque, gingivitis and oral malodor.

2. Description of the Prior Art

Oral malodor, gingivitis and periodontal disease are all undesirable conditions that effect many people. It is well known that these conditions are associated with an accumulation of dental plaque, which is formed by absorption and propagation of intraoral bacteria such as Streptococcus mutans and the like on the surfaces of the teeth. Therefore, it is important to remove dental plaque to prevent and treat the above-mentioned conditions.

The usual approach towards combating the accumulation of dental plaque is by mechanical ways, such as brushing and flossing. Even the most thorough mechanical cleaning fails to eliminate interproximal dental plaque. Furthermore, in practice, the majority of people fail to regularly conduct a sufficient cleaning and, therefore, the rate of diseases such as gingivitis and periodontal disease is not reduced despite mechanical cleaning. It therefore becomes necessary to complement mechanical oral hygiene measures with chemotherapeutic agents to inhibit the development of dental plaque.

U.S. Pat. No. 6,086,856 is directed to the use of oral hygiene formulations in foaming compositions for preventing plaque and gingivitis. The formulations comprise mouthwashes containing one or more antimicrobial agents, which may include cetylpyridinium chloride and domiphen bromide. In addition, this patent provides for a total concentration of antimicrobial agent in the range from about 0.005% to about 3% by weight of the formulation.

U.S. Pat. No. 4,959,204 is directed to the use of glycerin, sorbitol, ethyl alcohol, saccharin and sodium saccharin in dentifrice composition for preventing plaque and gingivitis. In addition, this patent provides for the inclusion of either a N-tetradecylpyridinium salt or a N-tetradecyl-4-ethylpyridinium salt for better gingival bleeding reduction.

U.S. Pat. No. 5,382,424 is directed to a microcapsule that has a composition, which includes sorbitol, saccharin, cetyl pyridinium chloride and domiphen bromide for reducing oral bacteria and providing breath protection.

U.S. Pat. No. 6,086,858 is directed to a foamable aqueous mouthwash. The mouthwash has the following components: glycerin, alcohol, polysorbate, saccharin, sorbitol, cetyl pyridiniom chloride and domiphen bromide.

SUMMARY OF THE INVENTION

It is an object of the present invention to provide a mouthspray formulation, that reduces oral bacteria, is effective against plaque, gingivitis and oral malodor and has a pleasant taste.

It is another object of the present invention to provide a mouthspray formulation having a bactericidal agent having cetyl pyridinium chloride and domiphen bromide.

It is still another object of the present invention to provide such a mouthspray formulation that has a ratio of cetyl pyridinium chloride to domiphen bromide of about 5 to about 1.

It is yet another object of the present invention to provide such a mouthspray formulation having a flavor system.

It is a further another object of the present invention to provide a mouthspray formulation that can be reliably and inexpensively manufactured.

These and other objects and advantages of the present invention are achieved by a mouthspray formulation that comprises a bactericidal agent having cetyl pyridinium chloride and domiphen bromide. The formulation preferably includes one or more of the following: an alcohol component, a sweetener component, and a flavor system. In one embodiment the flavor system has a flavorant, a humectant, a surfactant, a sweetener, and a colorant agent.

Other and further objects, advantages and features of the present invention will be understood by reference to the following specification.

DESCRIPTION OF THE INVENTION

The present invention is directed to a mouthspray formulation having a bactericidal agent. The bactericidal agent has cetyl pyridinium chloride and domiphen bromide. The formulation may also have one or more of the following: an alcohol component, a sweetener component and a flavor system.

According to the present invention, the bactericidal agent having cetyl pyridinium chloride and domiphen bromide is effective for combating the accumulation of dental plaque on the surface of the teeth. Additional agents known to be effective against microorganisms, which cause dental plaque, may also be included in the bactericidal agent.

These agents include quaternary ammonium salt compounds such as morpholinium tetradecylsulfate, lauryl pyridinium chloride, myristyl puridinium chloride, cetyl peridinium bromide, cetyl peridinium chloride, cetyl peridinium iodide, stearyl pyridinium chloride, dodecyltrimethyl ammonium chloride, hexadecyltrimethyl ammonium bromide, benzethonium chloride, domiphen bromide, triclobisonium chloride and other cationic agents such as chlorhexidine salts, zinc salts and copper salts, or any combinations thereof. In addition, non-cationic agents can be used, for example, triclosan.

The total amount of bactericidal agent may range from about 0.025 percentage by weight or weight percent (wt %) to about 0.075 wt % of the formulation. Preferably, cetyl pyridinium chloride is present in the bactericidal agent at about 0.05 wt % of the formulation, and domiphen bromide is present at about 0.01 wt % of the formulation. The ratio of cetyl pyridinium chloride to domiphen bromide is about 5:1.

Water is also a component of the mouthspray formulation. Water is present in the range from about 25 wt % to about 35 wt %, preferably about 30 wt % of the formulation. The water in the mouthspray formulation is separate from water that may be found in any other component of the system, such as the flavor system. The water used in the mouthspray formulation should be of low ion content and free of organic impurities.

The present formulation may include an alcohol. Alcohols that are suitable in the present invention include, but are not limited to denatured ethanol SD37, denatured ethanol SD37A, denatured ethanol SD38B (SD alcohol 38B), and denatured ethanol SD38A-F. A preferred alcohol is SD alcohol 38B. The amount of alcohol in the present formulation is about 40 wt % to about 50 wt %. Preferably, the amount of alcohol is about 46.92 wt % of the formulation.

In accordance with one embodiment of the present invention, the formulation may also have a sweetener component. The sweetener component is used to enhance the desirable pleasant taste of the formulation. The sweetener component may include sucrose, glucose, saccharin, dextrose, levulose, lactose, mannitol, sorbitol, fructose, maltose, xylitol, thaumatin, aspartame, D-tryptophan, dihydrochalcones, acesulfame, and any combinations thereof. The preferred sweetener component is saccharin.

The formulation may have an amount of sweetener component from about 0.8 wt % to about 1.5 wt %, and preferably about 1.20 wt % of the formulation.

The mouthspray formulation may also have a flavor system. The flavor system may have one or more of the following: a humectant, a surfactant, an alcohol, a flavorant, a sweetener, and a colorant agent, as well as water.

The amount of flavor system in the present formulation is about 25 wt % to about 30 wt %. The preferred amount of flavor system component in the mouthspray formulation is about 28.5 wt %.

A humectant adds body to the mouthspray formulation and retains moisture in a dentifrice composition. In addition, a humectant helps to prevent microbial deterioration during storage of the formulation. It also assists in maintaining phase stability and provides a way to formulate a transparent or translucent dentifrice. A humectant, for use in the flavor system, may be one or more of the following: propylene glycol, glycerin, erythritol, xylitol, sorbitol, mannitol, lactitol, hydrogenated starch hydrolyzates, or any combinations thereof.

The preferred humectants for use in the flavor system are glycerin and sorbitol. The preferred amount of glycerine in the flavor system is about 15 wt % to about 25 wt % of the formulation. The preferred amount of sorbitol in the flavor system is less than 1 wt % of the formulation.

According to the present invention, the flavor system may have a surfactant. The surfactant preferably is a nonionic surfactant in order to solubilize flavor. Suitable nonionic surfactants include one or more of the following: polysorbate (20), polysorbate (40), polysorbate (60), polysorbate (60K), polysorbate (60VS), polysorbate (65), polysorbate (80), or any combinations thereof. The most preferred surfactant is polysorbate (20).

The preferred amount of surfactant in the flavor system is about from 0.5 wt % to about 1.5 wt %, and preferably less than 1 wt % of the formulation.

The flavor system may have a natural or an artificial flavorant. The examples of flavorants that can be used in the present formulation include oils of anise, caraway, clove, coriander, eculyptol, eucalyptus, euguanol, irone, methyl salicylate, menthol, orris, pimento, thymol, witch hazel, or any combinations thereof. The preferred flavorant is menthol.

The preferred amount of flavorant in the flavor system is about 1 wt % to about 5 wt %, and more preferably 3.5 wt % of the formulation.

The flavor system may have a sweetener. The sweetener may be any sweetener described above. However, the preferred compound is sodium saccharin. The amount of the sweetener in the flavor system is preferably less than 2 wt % of the formulation.

It is preferable, according to the present invention, to add a colorant agent to the mouthspray formulation. The colorant agent may be one or more of the following: D&C blue #1 and #5, D&C brown #1, D&C green #5 through #8, D&C orange #4 through #11, D&C red #6 through #40, FD&C blue #1, #2 and #4, FD&C red #3, #4, #33 and #40, FD&C yellow #5, #6 and #10, FD&C orange #4, FD&C green #3, carmine, or any combinations thereof. The preferred colorant agent is FD&C blue #1.

The amount of the colorant agent in the flavor system is about 0.004 wt % to about 0.006 wt %, and preferably less than 0.01 wt % of the formulation.

In addition to the above-described constituents, the flavor system has about 10 wt % to about 14 wt % of water and about 79 wt % to about 83 wt % of ethyl alcohol.

The mouthspray formulation of the present invention may also have additional constituents, which may include, but are not limited to, one or more desensitizing agents, healing agents, chelating agents, vitamins, amino acids, proteins, other agents capable of reducing dental plaque accumulations, antibiotics, oxidizing agents, pH control agents, whitening agents, enzymes, or any combinations thereof.

The following Example further describes and demonstrates the preferred embodiment of the present invention. The Example is given solely for the purpose of illustration and is not to be construed as limiting the present invention since many variations are possible without departing from the spirit and scope of the invention.

EXAMPLE

All ingredients in Table 1 are mixed at room temperature in the order shown below.

TABLE 1

| Ingredients | Wt % for total composition |
|---|---|
| flavor system | 25.10% |
| denatured alcohol 38B | 43.74% |
| saccharin | 1.10% |
| cetyl pyridinium chloride | 0.05% |
| domiphen bromide | 0.01% |
| water | 30.00% |

The flavor system of Table 1 includes the ingredients shown in Table 2.

TABLE 2

| Ingredients | Wt % for total composition |
|---|---|
| glycerin | 15–20% |
| ethyl alcohol | 79–84% |
| flavorant | 1–5% |
| water | 10–15% |
| polysorbate 20 | <1% |
| sodium saccharin | <1% |
| sorbitol | <1% |
| FD&C Blue No. 1 | <0.01% |

It should be understood that various alternatives and modifications can be devised by those skilled in the art, and the present invention can be applied to other types of mouthspray formulations. The present invention is intended to embrace all such alternatives, modifications and variances that fall within the scope of the appended claims.

What is claimed is:

1. A mouthspray formulation comprising:
   an alcohol; and
   a bactericidal agent,
   wherein said bactericidal agent is cetyl pyridinium chloride and domiphen bromide in a ratio of about 5 to about 1.

2. The mouthspray formulation of claim 1, wherein said bactericidal agent is present in an amount about 0.04 wt % to about 0.08 wt %.

3. The mouthspray formulation of claim 1, wherein said bactericidal agent comprises about 0.05 wt % cetyl pyridinium chloride and about 0.01 wt % domiphen bromide.

4. The mouthspray formulation of claim 1, wherein said alcohol is selected from the group consisting of denatured ethanol SD37, denatured ethanol SD37A, denatured ethanol SD38B and denatured ethanol SD38A-F, and any combinations thereof.

5. The mouthspray formulation of claim 1, wherein said alcohol is present in an amount about 40 wt % to 50 wt %.

6. The mouthspray formulation of claim 1, further comprising a sweetener component.

7. The mouthspray formulation of claim 6, wherein said sweetener component is selected from the group consisting of sucrose, glucose, saccharin, dextrose, levulose, lactose, mannitol, sorbitol, fructose, maltose, xylitol, thaumatin, aspartame, D-tryptophan, dihydrochalcones, acesulfame, and any combinations thereof.

8. The mouthspray formulation of claim 6, wherein said sweetener component is saccharin.

9. The mouthspray formulation of claim 6, wherein said sweetener component is present in an amount about 0.08 wt % to about 1.5 wt %.

10. The mouthspray formulation of claim 1, further comprising a flavor system.

11. The mouth spray formulation of claim 10, wherein said flavor system is present in an amount about 25 wt % to about 30 wt %.

12. The mouthspray formulation of claim 10, wherein said flavor system comprises a flavorant, a humectant, a surfactant, a sweetener and a colorant agent.

13. The mouthspray formulation of claim 12, wherein said flavorant is selected from the group consisting of oils of anise, caraway, clove, coriander, eculyptol, eucalyptus, euguanol, irone, mathyl salicylate, menthol, orris, pimento, thymol, witch hazel, and any combinations thereof.

14. The mouthspray formulation of claim 12, wherein said flavorant is present in an amount about 1 wt % to about 5 wt %.

15. The mouthspray formulation of claim 12, wherein said humectant is selected from the group consisting of propylene glycol, glycerin, erythritol, xylitol, sorbitol, mannitol, lactitol, hydrogenated starch hydrolyzates, and any combinations thereof.

16. The mouthspray formulation of claim 12, wherein said humectant comprises glycerin and sorbitol.

17. The mouthspray formulation of claim 16, wherein said glycerin is present in an amount about 79 wt % to 84%, and wherein and said sorbitol is present in an amount less than 1 wt %.

18. The mouthspray formulation of claim 12, wherein said surfactant is selected from the group consisting of polysorbate (20), polysorbate (40), polysorbate (60), polysorbate (60K), polysorbate (60VS), polysorbate (65), polysorbate (80), and any combinations thereof.

19. The mouthspray formulation of claim 12, wherein said surfactant is present in an amount less than 1 wt %.

20. The mouthspray formulation of claim 12, wherein said sweetener is present in an amount less than 1 wt %.

21. The mouthspray formulation of claim 12, wherein said colorant agent is selected from the group consisting of D&C blue #1 and #5, D&C brown #1, D&C green #5 through #8, D&C orange #4 through #11, D&C red #6 through #40, FD&C blue #1, #2 and #4, FD&C red #3, #4, #33 and #40, FD&C yellow #5, #6 and #10, FD&C orange #4, FD&C green #3, carmine, and any combinations thereof.

22. The mouthspray formulation of claim 12, wherein said colorant agent is present in an amount less than 0.01 wt %.

23. The mouthspray formulation of claim 12, wherein said flavor system further comprises an ethyl alcohol.

24. The mouthspray formulation of claim 23 wherein said ethyl alcohol in said flavor system is present in an amount about 8 wt % to about 13 wt %.

25. The mouthspray formulation of claim 12, wherein said flavor system further comprises water.

26. The mouthspray formulation of claim 25, wherein said water is present in an amount about 1 wt % to about 5 wt %.

27. The mouth spray formulation of claim 1, further comprising water.

28. The mouth spray formulation of claim 27, wherein the water is present in an amount about 25 wt % to about 35 wt %.

29. A mouthspray formulation for combating dental plaque, oral bacteria, gingivitis and oral malodor comprising a bactericidal agent having cetyl pyridinium chloride and domiphen bromide in a ratio of about 5 to about 1, an alcohol, a sweetener component, and a flavor system.

* * * * *